United States Patent [19]
Lam

[11] Patent Number: 5,382,240
[45] Date of Patent: Jan. 17, 1995

[54] CANNULA GUARD

[75] Inventor: David Lam, Walnut, Calif.

[73] Assignee: Precision Dynamics Corporation, San Fernando, Calif.

[21] Appl. No.: 192,201

[22] Filed: Feb. 4, 1994

Related U.S. Application Data

[63] Continuation of Ser. No. 640,709, Jan. 14, 1991, abandoned.

[51] Int. Cl.6 .............................................. A61M 5/00
[52] U.S. Cl. .................... 604/177; 604/171; 604/110; 604/198; 604/263; 604/53
[58] Field of Search ............... 604/177, 171, 164–165, 604/162, 110, 53, 263, 198; 128/919, DIG. 26

[56] References Cited

U.S. PATENT DOCUMENTS

| | | | |
|---|---|---|---|
| 3,658,061 | 4/1972 | Hall . | |
| 4,192,304 | 3/1980 | Millet | 604/177 X |
| 4,194,504 | 3/1980 | Harms et al. | 604/177 X |
| 4,388,074 | 6/1983 | Seberg et al. | 604/165 |
| 4,664,259 | 5/1987 | Landis | 206/365 |
| 4,676,983 | 6/1987 | Jagger et al. | 604/171 |
| 4,747,836 | 5/1988 | Luther | 604/198 |
| 4,775,369 | 10/1988 | Schwartz | 604/263 |
| 4,778,453 | 10/1988 | Lopez | 604/110 |
| 4,781,692 | 11/1988 | Jagger et al. | 604/164 |
| 4,782,841 | 11/1988 | Lopez | 128/164 |
| 4,820,282 | 4/1989 | Hogan | 604/263 |
| 4,850,961 | 7/1989 | Wanderer et al. | 604/53 |
| 4,867,172 | 9/1989 | Haber et al. | 128/763 |
| 4,888,001 | 12/1989 | Schoenberg | 604/162 |
| 4,898,589 | 2/1990 | Dolgin et al. | 604/198 |
| 4,935,011 | 6/1990 | Hogan | 604/177 |
| 4,943,281 | 7/1990 | Kothe | 604/192 |
| 4,969,876 | 11/1990 | Patterson | 604/171 |
| 4,991,881 | 7/1990 | Masters et al. | 604/162 |
| 5,019,049 | 5/1991 | Hairing | 604/165 |
| 5,067,946 | 11/1991 | Zhadanov | 604/198 |
| 5,085,639 | 2/1992 | Ryan | 604/110 |
| 5,088,982 | 2/1992 | Ryan | 604/110 |
| 5,108,376 | 4/1992 | Benaldo | 604/171 |
| 5,112,311 | 5/1992 | Utterberg et al. | 604/177 |
| 5,112,312 | 5/1992 | Luther | 604/177 |
| 5,120,320 | 6/1992 | Fayngold | 604/177 |
| 5,135,505 | 8/1992 | Kaufman | 604/165 |
| 5,167,635 | 12/1992 | Haber et al. | 604/164 |
| 5,171,231 | 12/1992 | Heiliger | 604/263 |
| 5,176,655 | 1/1993 | McCormick et al. | 604/198 |
| 5,192,275 | 3/1993 | Burns | 604/263 |
| 5,201,713 | 4/1993 | Rossetti | 604/165 |
| 5,215,525 | 6/1993 | Sturman | 604/164 |
| 5,219,339 | 6/1993 | Saito | 604/158 |

FOREIGN PATENT DOCUMENTS 9003196  4/1990  WIPO ................................ 694/177

Primary Examiner—C. Fred Rosenbaum
Assistant Examiner—Perry E. Van Over
Attorney, Agent, or Firm—J. Mark Holland; Thomas P. Mahoney

[57]  ABSTRACT

A guard for a cannula is characterized by an outer tubular sheath slidably disposed about the cannula. The tubular sheath includes first engagement tabs to engage the cannula and facilitate insertion of the cannula into a patient. Simultaneously with removal of the cannula from the patient, the cannula and specifically its distal end may be slidably withdrawn into the outer sheath. Second engagement tabs permit permanent retention of the distal end of the cannula within the outer sheath. The first engagement tabs are preferably demountable from the sheath to facilitate ease of disposal of the used components.

13 Claims, 3 Drawing Sheets

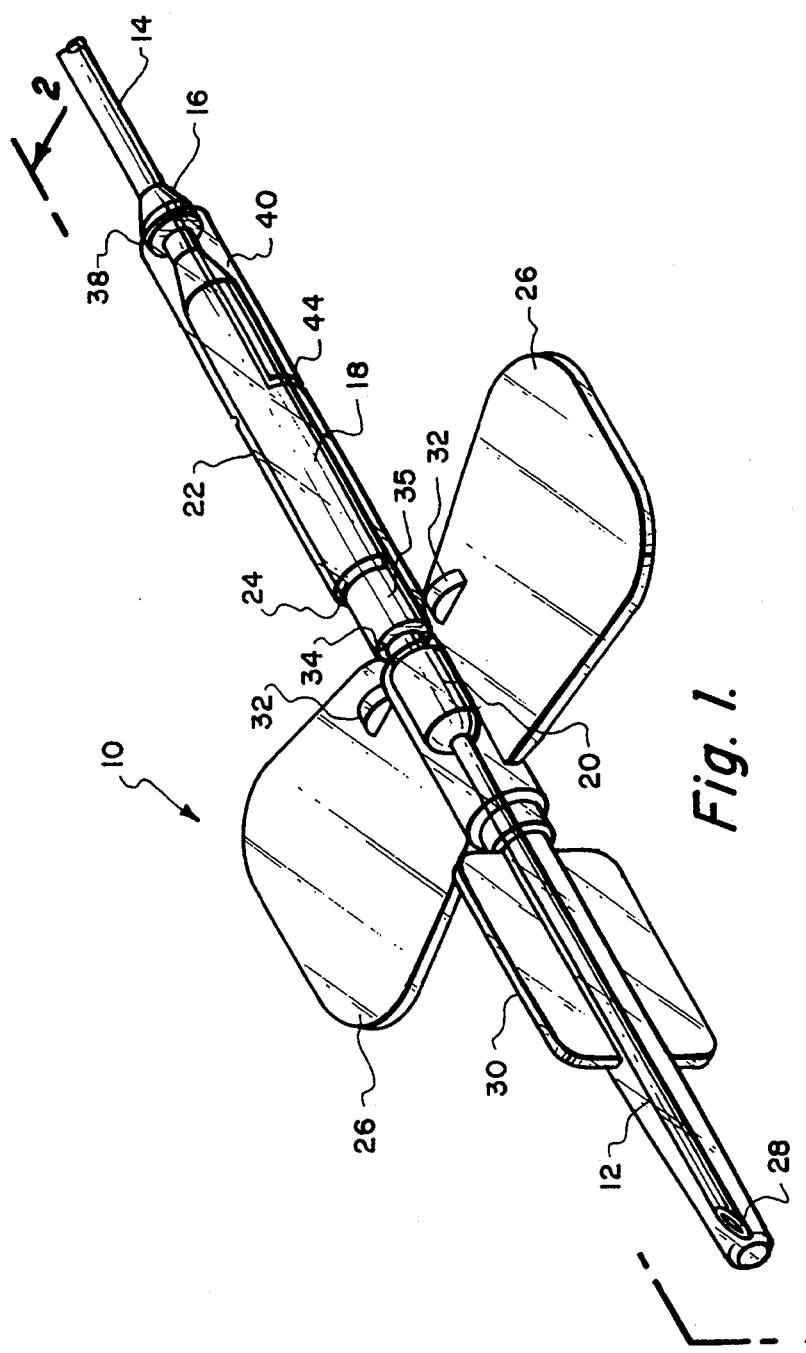
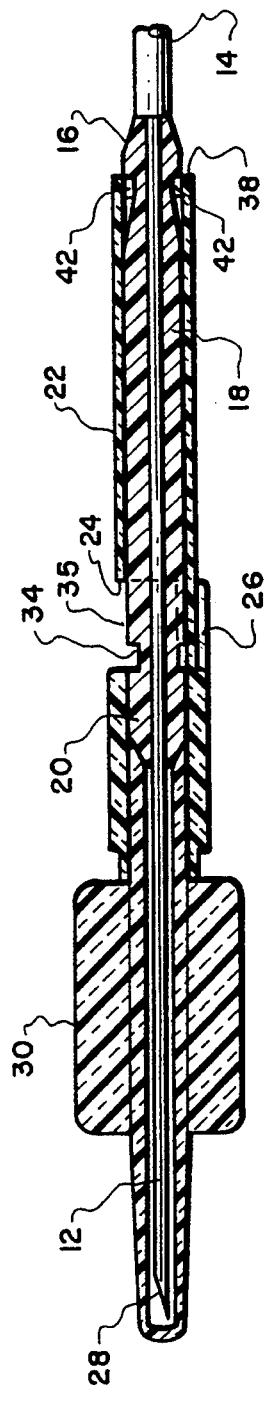

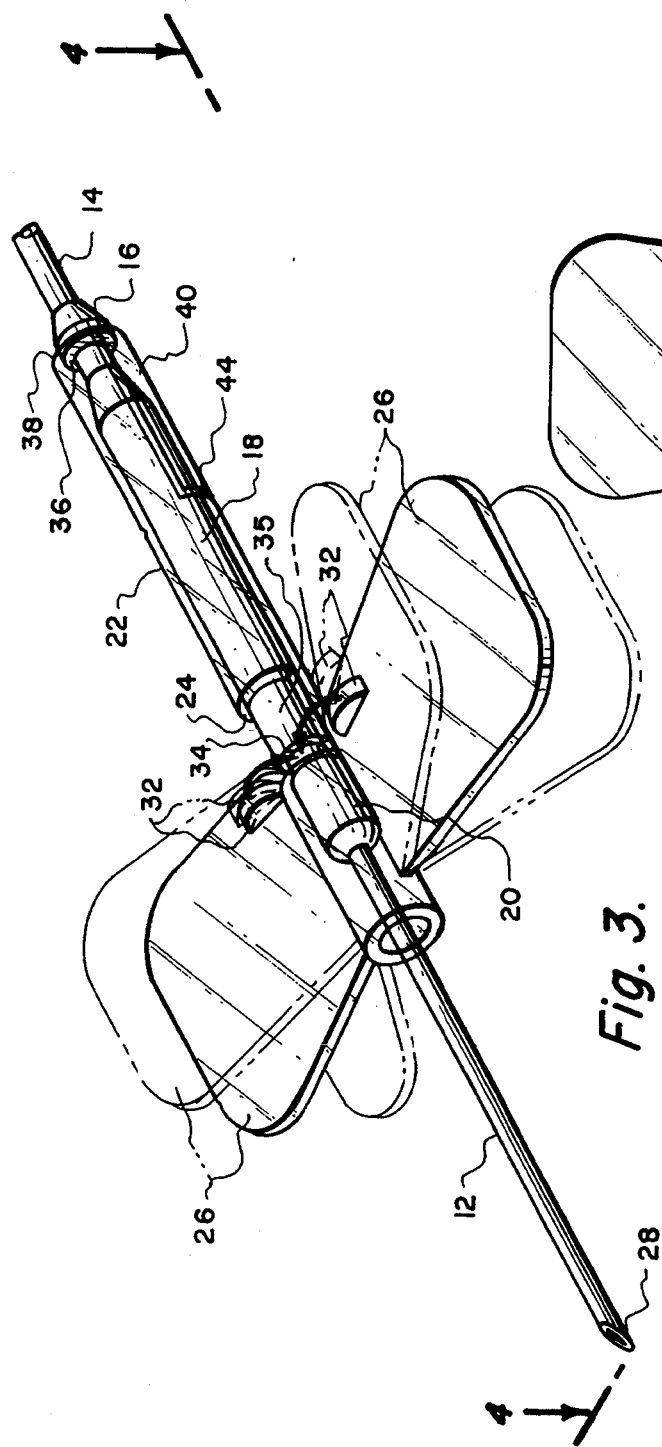
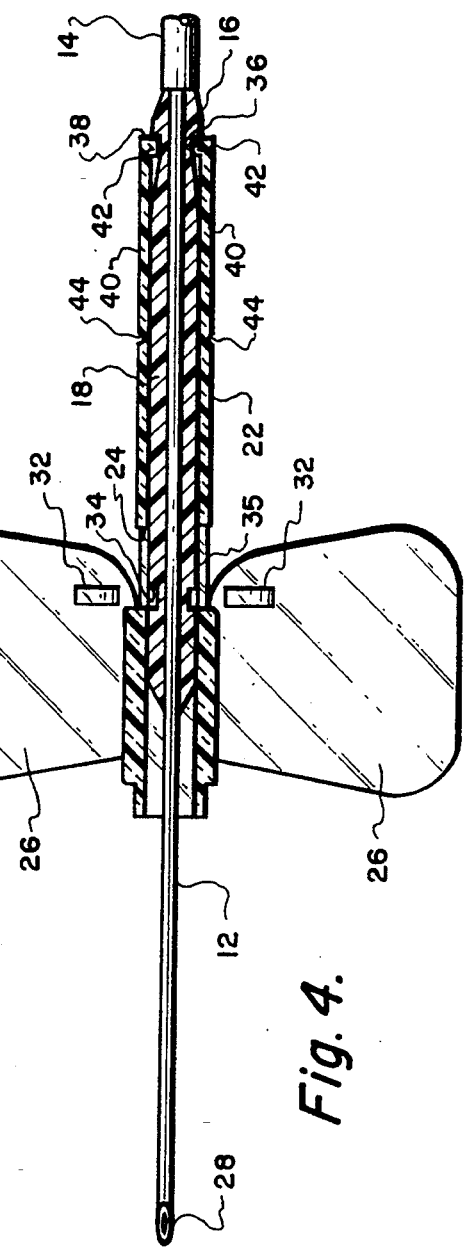
Fig. 3.
Fig. 4.

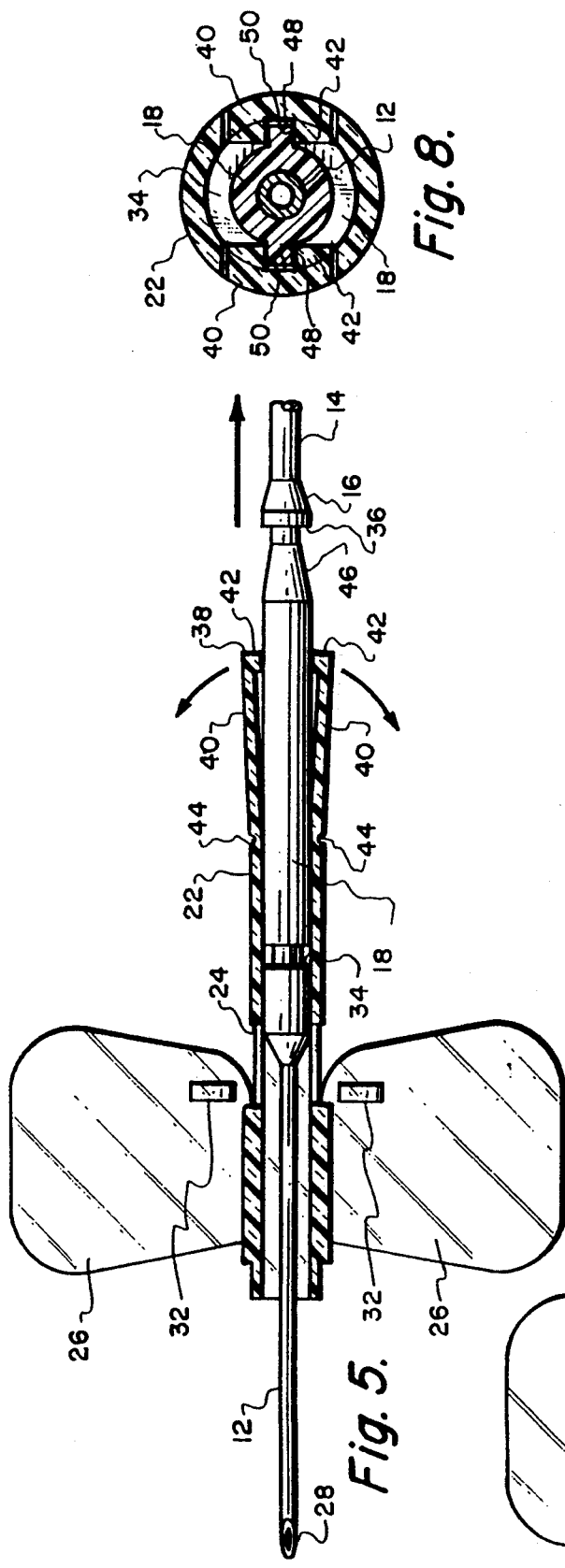
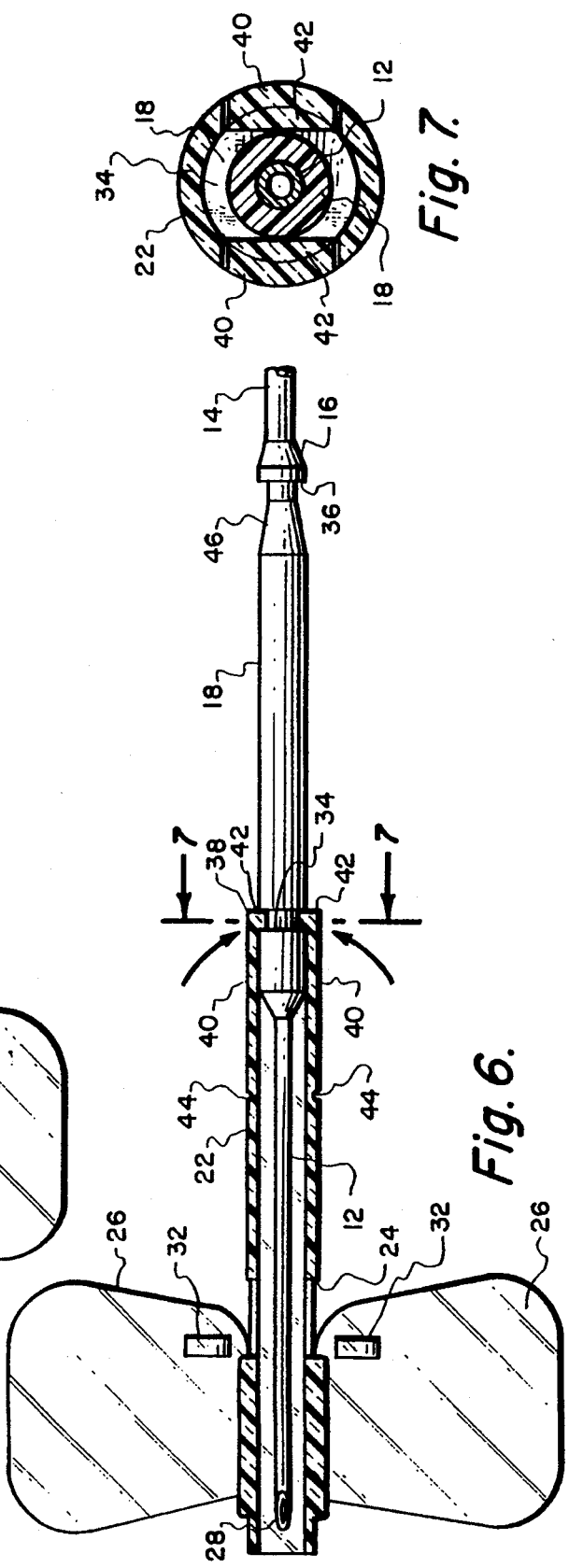

CANNULA GUARD

This application is a continuation of application Ser. No. 07/640,709, filed on Jan. 4, 1991, now abandoned.

BACKGROUND OF THE INVENTION

This invention generally relates to safety guards for cannular devices, and specifically to a cannula guard useful in taking blood donations, performing blood transfusions, administering medication or the like. The guard of the invention is characterized by an outer sheath member slidably disposed about the cannula. The outer sheath may be operably engaged with the cannula to facilitate insertion of the cannula into a patient, and when the cannula is withdrawn from the patient, the same motion retracts the cannula (including specifically the exposed distal tip thereof) within the outer sheath and accomplishes permanent retention of the distal tip within the outer sheath.

Numerous devices have been proposed to reduce the danger of handling potentially contaminated needles, cannulas and the like. It is well known that, for example, handling and disposal of used cannular needles exposes nurses, doctors and other persons to the risk that they will be pricked by the pointed, distal end of the needle and possibly become infected with AIDS or another disease.

Among the devices presently available to address this problem are U.S. Pat. Nos. 4,778,453 and 4,782,841 to Lopez, and U.S. Pat. No. 4,820,282 to Hogan. The Lopez patents disclose guards usable with hypodermic syringes and require that the needle assemblies be screwed onto the syringe. For that reason, the Lopez guards are not readily adaptable for use in cannular applications. Moreover, the devices of the Lopez patents leave a substantial portion of the used needle exposed to subsequent handlers of the assembly, and the '841 patent even leaves the proximate end of its needle 26 in a dangerously unprotected state after removal from the syringe.

The well-known use of "butterfly needles" is illustrated in the Hogan '282 patent. The guard of Hogan has significant shortcomings, however, including the facts that the guard is separate from the "butterfly" structure rather than being packaged and utilized as a single unit, and that the manipulation of the guard during its use may cause substantial, and predictably painful or uncomfortable, movement of the cannula within the patient's body.

Our invention, in contrast, provides the simplicity of a single unitized butterfly needle and guard, and accomplishes substantially complete coverage of the used needle virtually immediately upon withdrawal of the needle from the patient.

OBJECTS AND ADVANTAGES OF THE INVENTION

It is, therefore, an object of our invention to provide a cannular guard device which is characterized by its incorporation of traditional "butterfly needle" features and benefits while providing a relatively permanent and safe covering for the cannula after use, in order to protect against subsequent contact or contamination by the cannula.

The cannula guard of our invention preferably includes a tubular outer sleeve or sheath member slidably disposed around the cannula. After removal of a cover from the distal tip of the cannula, butterfly- or wing-shaped strips attached to or demountably associated with the sheath member are gripped in the normal manner to manipulate the cannula for insertion. The butterfly- or wing-shaped strips of our invention preferably include engagement tabs on the inner surfaces thereof to engage the cannula, thereby permitting controlled manipulation of the cannula and needle during insertion and reducing or eliminating any relative sliding movement between the sheath and the cannula.

In a typical application, after insertion of the cannula, the butterfly strips are taped to the patient's body to minimize movement of the cannula assembly with respect to the patient. When removing the cannula from the patient's body after use, the potentially contaminated distal tip may be simultaneously retracted into and retained within the sheath, minimizing any risk that subsequent handling of the assembly will cause injury or infection.

Another object of the invention is the provision of a cannular guard which may be readily utilized by personnel without the need for substantial training. As noted above, the device of our invention incorporates a similar physical structure as in presently utilized butterfly needles, and the use of our invention entails relatively minor departures from that of such needles.

An additional object of our invention is the provision of a guard of the aforementioned character which is relatively easy to manufacture, package and handle. The various components are readily fabricated through injection- or insert-molding processes or the like. Prior to disposal, the "butterfly wings" of the preferred embodiment may be removed from the remainder of the assembly to facilitate such disposal.

Moreover, because of the unitary nature of the guard assembly of our invention, personnel utilizing the device do not have to search for or assemble any components when using the device of our invention.

Yet another object of our invention is the provision of a guard of the aforementioned character which incorporates cannular means having a distal end for insertion in a patient and a proximate end operably connected to fluid receiving means and an outer sheath member slidably disposed about said cannular means. First engagement means is preferably provided for engaging the cannular means and the outer sheath member with one another to enable insertion of said distal end of the cannula into the patient. Second engagement means is provided for retaining said distal end of the cannular means within the outer sheath member after said distal end has been slidably retracted thereinto.

Still another object of our invention is the provision of a needle guard for covering a hollow needle after insertion and removal of said needle from a patient which includes a first tubular member having first and second ends thereof with the needle operatively affixed to said first end whereby fluid may flow from the patient through the needle, then through the first end of the first tubular member, and finally through the second end of the first tubular member. A second tubular member is slidably disposed about the first tubular member, and first engagement means engaging the second tubular member with said first tubular member facilitates the insertion of the needle. Second engagement means permanently engages the first tubular member with the second tubular member after the needle has been positioned within the second tubular member.

Other objects and advantages of the invention will be apparent from the following specification and the accompanying drawings, which are for the purpose of illustration only.

BRIEF DESCRIPTION OF THE DRAWINGS

FIG. 1 is an isometric view of a cannula guard assembly constructed in accordance with the teachings of the invention;

FIG. 2 is a partially sectional view, taken along line 2—2 of FIG. 1;

FIG. 3 is an isometric view of the cannula guard of FIG. 1, having the distal end of the cannula exposed and indicating the flexibility of wing-shaped gripping members;

FIG. 4 is a partially sectional view, taken along line 4—4 of FIG. 3;

FIG. 5 is a view similar to FIG. 4, illustrating the sliding retraction of the cannula within an outer sheath member;

FIG. 6 is a view similar to FIG. 5, illustrating the completed retraction of the cannula into the outer sheath member;

FIG. 7 is a sectional view, taken along line 7—7 of FIG. 6; and

FIG. 8 is a sectional view similar to FIG. 7, illustrating an alternative embodiment of the invention.

DESCRIPTION OF PREFERRED EMBODIMENT

Referring to the drawings, and particularly to FIGS. 1 and 2 thereof, I show a cannula guard assembly 10 constructed in accordance with the teachings of the invention and including cannular means such as a stainless steel needle 12 operably affixed to fluid receiving means such as a flexible tube 14. Although many of the components illustrated in the drawings are shown as transparent or in phantom, those skilled in the art will understand that such representation facilitates this disclosure and is not intended as a limitation regarding the opacity of the various materials to be utilized in the invention.

In the preferred embodiment, the needle 12 is attached to the tube 14 at a neck 16. The section of the needle 12 adjacent the neck 16 is coated or otherwise molded, such as through an insert- or injection-molding process, with a plastic or other suitable annular layer 18. A preferred material for this coating is polypropylene, although any of a wide variety of materials may be utilized with efficacy. Various structural features of the outer surface of the coating 18, and the utility thereof, are discussed below.

In an alternative embodiment, the annular coating 18 may constitute a first tubular member 18, with the needle 12 operably affixed to a first end 20 of the tubular member 18, and the neck 16 constituting a second end of the tubular member 18. In such an alternative embodiment, the cannular means 12 does not extend through the length of the cannula guard assembly 10, but instead terminates in an intermediate portion thereof.

A second tubular member such as a sheath 22 is slidably disposed about the cannular means 12 and preferably in contiguous relationship with the coating 18. The sheath 22 may be fabricated from polypropylene, polyethylene or some other suitable material. The sheath includes an opening 24 along one side thereof.

The assembly further preferably includes gripping means such as butterfly-shaped or wing-shaped strips 26 operably associated with the sheath 22. In the preferred embodiment, the gripping means 26 is fabricated from polyethylene or a similar material and is demountable from the sheath, although those skilled in the art will understand that the wing-shaped strips may be permanently affixed or even integrally molded with the sheath 22.

The wing-shaped strips 26 preferably include projections 32 positioned to be cooperatingly received in a necked-down portion 34 or similar expedient on the coating 18. As illustrated in FIG. 3, the strips 26 may be readily raised upwardly into contiguous relationship with one another, thereby engaging the projections 32 are operably disposed in the necked-down portion 34. In such a position, the assembly 10 may be readily manipulated to insert the distal end 28 of the needle 12 into a patient, by grasping the wings 26. The engagement of the projections 32 in the necked-down portion 34 precludes axial displacement of the cannular means with respect to the gripping means 26.

Also shown in FIGS. 1 and 2 is a removable cover 30 for the distal end 28 of the needle 12. The cover 30 is provided for protective purposes during transport and initial handling of the assembly, but is removed prior to use of the cannula, resulting in a structure such as that shown in FIGS. 3–6.

After insertion of the cannula into a patient, the butterfly strips may be utilized in a conventional manner to maintain the cannula assembly in a fixed position on the patient's arm, such as by juxtaposing the wings 26 with the patient's skin and placing adhesive tape across the assembly and the patient's adjacent skin.

In a preferred use of the invention, the same or additional strips of tape are placed across the opening 24 and operably adhered to a surface 35 of the coating 18 adjacent the necked-down portion 34. By this or a similar expedient, additional stability and resistance to movement is provided to the assembly while in use. Of course, prior to removing the cannula from the patient's arm (as more thoroughly described below), the tape or other expedient should then be disengaged from the surface 35 to facilitate the sliding removal of the cannula from the sheath.

Those skilled in the art will understand that a wide variety of retention means, such as the aforedescribed combination of the opening 24, the surface 35, and operably located adhesive tape (not shown), may be effectively utilized to accomplish the desired purpose without departing from the teachings of the invention.

As best shown in FIG. 5, the aforementioned various structural features of the coating 18 include a land 36 adjacent the neck 16. The end 38 of the outer sheath 22 further includes engagement tabs 40 pivotable at detents 44 or otherwise flexible as necessary to achieve the functions described below and having engaging portions 42 disposed on the inward surfaces thereof. As originally provided, FIGS. 1–4, the engaging portions 42 abut the land 36 to prevent dislodgement of the sheath 22 over the tube 14.

After use of the cannula has been completed, the distal end 28 of the needle 12 is removed from the patient by pulling on the tube 14, as indicated in FIGS. 4–6. During such pulling manipulation, the butterfly strips 26 are preferably held in place on the patient's skin by the aforementioned tape and/or light pressure from an attendant's hand. Thus, the inner cannular needle 12 and its coating or tube member 18 is slidingly displaced with respect to the outer sleeve or sheath 22.

During this sliding action and as a result thereof, the engaging portions 42 ride up the ramped surface 46 of the coating or tube 18, effectively spreading the flexible engagement tabs or fingers 40 to permit the desired sliding withdrawal of the needle within the sheath 22.

An intermediate stage of such withdrawal is illustrated in FIG. 5. As shown in FIG. 6, such sliding withdrawal eventually results in the engagement of the engaging portions 42 of the flexible engagement tabs or fingers 40 with the slot or necked-down portion 34. In this position, the distal end 28 of the needle is contained within the sheath 22 and inadvertent pricking or other contact with the end are avoided. Utilization of appropriate materials for the various components can result in effective "permanent" retention of the distal end 28 of the needle in this position.

The preferred internal configuration of the engaging portions 42 is illustrated in FIG. 7. An internal cooperating means such as illustrated in FIG. 8 may be provided on the engaging portions 42 to prevent rotation of the sheath about the lengthwise axis of the needle 12. To prevent such rotation when the assembly is in the permanent configuration, FIG. 6, projections such as projections 48 may be provided at the necked-down portion 34. Cooperating slots 50 operatively receive the projections 48 and preclude the undesirable rotation. Similar projections may also be provided, of course, adjacent the land 36 and ramped surface 46 to preclude such rotation prior to utilization of the assembly. Through simple modification, not shown, such rotation could likewise be prevented during the entire retraction of the needle 12 within the sheath 22.

Thus, by our invention, we provide a simple device to reduce the risks associated with utilization of cannular devices. The distal end 28 of the cannular needle may be "permanently" sheathed virtually immediately upon removal of the cannula from the patient's body.

The cannula guard of our invention has been described with some particularity but the specific designs and constructions disclosed are not to be taken as delimiting of the invention in that various modifications will at once make themselves apparent to those of ordinary skill in the art, all of which will not depart from the essence of the invention and all such changes and modifications are intended to be encompassed within the appended claims.

We claim:

1. In a cannula guard assembly, the combination of: cannular means having a distal end for insertion in a patient and a proximate end operably connected to fluid receiving means; an outer sheath member slidably disposed about said cannular means, said sheath member having a first end and a second end and further having an opening in said sheath member disposed between said first and second ends; first engagement means for establishing interlocking engagement between said cannular means and said outer sheath member and second engagement means for retaining said distal end of said cannular means within said outer sheath member after said distal end has been slidably retracted thereinto, in which said outer sheath member includes gripping means associated therewith and in which said first engagement means include projecting portions operably disposed on said gripping means and selectively movable from a first non-engaged position to a second position in which said projecting portions extend through said opening and engage in corresponding receiving portions on said cannular means.

2. The assembly of claim 1, in which said gripping means is demountable from said outer sheath member.

3. The assembly of claim 1 or claim 2, including retention means for retaining said cannular means in a relatively fixed position with respect to said patient, after insertion of said cannular means into said patient and prior to said retraction of said distal end into said outer sheath, said retention means including said opening in said outer sheath member, said opening being positionable so that a single strip of adhesive material may be adhered to said patient, across said opening onto said cannular means, and to said outer sheath.

4. The assembly of claim 1 or claim 2, in which said second engagement means includes flexible engagement tabs engageable with receiving portions on said cannular means.

5. The assembly of claim 1 or claim 2, in which said second engagement means includes flexible engagement tabs.

6. The assembly of claim 5, in which said flexible engagement tabs are adapted to permit said slidable retraction of said distal end into said outer sheath member and to subsequently engage said corresponding receiving portions on said cannular means.

7. In a needle guard for covering a hollow needle after insertion and removal of the needle from a patient, the combination of: a first tubular member having first and second ends thereof, the needle operatively affixed to said first end whereby fluid may flow from said patient through the needle then through said first end of said first tubular member and finally through said second end of said first tubular member; a second tubular member slidably disposed about said first tubular member, said tubular member having a first end and a second end and further having an opening therein between said first and second ends; first engagement means for establishing temporary interlocking engagement of said second tubular member with said first tubular member; and second engagement means for permanently engaging said first tubular member with said second tubular member after said first tubular member and the needle affixed thereto have been actuated to position the needle within said second tubular member, in which said second tubular member includes gripping means associated therewith constituted by butterfly-shaped strips, and in which said first engagement means include projecting portions operably disposed on said gripping means and selectively movable from a first non-engaged position to a second position in which said projecting portions extend through said opening and engage in corresponding receiving portions on said first tubular member.

8. The guard of claim 7, in which said gripping means is demountable from said second tubular member.

9. The guard of claim 7 or claim 8, in which said second engagement means includes flexible engagement tabs engageable with receiving portions on said first tubular member.

10. The guard of claim 7 or claim 8, in which said second engagement means includes flexible engagement tabs.

11. The guard of claim 10, in which said flexible engagement tabs are adapted to permit said slidable retraction of said distal end into said second tubular member and to subsequently engage said corresponding receiving means on said first tubular member, whereby said retention of said distal end in said second tubular member is achieved.

12. The guard of claim 7 or claim 8, including retention means for retaining the needle in a relatively fixed position with respect to said patient, after insertion of the needle into said patient and prior to said actuation of the needle into said second tubular member.

13. In a cannula guard assembly, the combination of: cannular means having a distal end for insertion in a patient and a proximate end operably connected to fluid receiving means; an outer sheath member slidably disposed about said cannular means and having gripping means thereon and further having first and second ends and an opening therebetween; first engagement means for engaging said cannular means and said outer sheath member with one another, said first engagement means including one or more projecting members external to said sheath member and disposed on said gripping means whereby sufficient flexure of said gripping means inserts said one or more projecting members through said opening in said outer sheath member; and second engagement means for retaining said distal end of said cannular means within said outer sheath member after said distal end has been slidably retracted thereinto, in which said second engagement means includes flexible engagement tabs.

* * * * *